US008097604B2

(12) United States Patent
Schramm

(10) Patent No.: US 8,097,604 B2
(45) Date of Patent: Jan. 17, 2012

(54) COMBINATION OF GESTAGEN AND INSULIN SENSITIZER FOR TREATING PCOS

(75) Inventor: Georg Schramm, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/325,529

(22) Filed: Dec. 1, 2008

(65) Prior Publication Data

US 2009/0118245 A1    May 7, 2009

Related U.S. Application Data

(63) Continuation of application No. PCT/EP2007/004700, filed on May 26, 2007.

(30) Foreign Application Priority Data

Jun. 1, 2006  (DE) .......................... 10 2006 026 026

(51) Int. Cl.
*A61K 31/56* (2006.01)
(52) U.S. Cl. ........................................ 514/170; 514/171
(58) Field of Classification Search .................. 514/170, 514/171
See application file for complete search history.

(56) References Cited

U.S. PATENT DOCUMENTS

| 2004/0029784 | A1 | 2/2004 | Hathaway | |
|---|---|---|---|---|
| 2004/0157809 | A1 | 8/2004 | De Zegher | |
| 2004/0248934 | A1* | 12/2004 | Chang | 514/310 |
| 2005/0187267 | A1 | 8/2005 | Hamann | |

FOREIGN PATENT DOCUMENTS

| DE | 102004026679 A1 | 12/2005 |
|---|---|---|
| WO | 2005115350 A | 12/2005 |

OTHER PUBLICATIONS

English Language Abstract for WO 2005/115350, 2005.
American College of Obstetricians and Gynecologists: "ACOG Practice Bulletin. Clinical Management Guidelines for Obstetrician-Gynecologists: No. 41, Dec. 2002." Obstetrics and Gynecology Dec. 2002, vol. 100, No. 6, Dec. 2002, pp. 1389-1402.
Pfeifer S M et al: "Treatment of the adolescent patient with polycystic ovary syndrome", Infertility and Reproductive Medicine Clinics of North America 2003 United States, vol. 14, No. 1, 2003, pp. 87-102.
Hardiman P et al: "Polycystic ovary syndrome and endometrial carcinoma" Lancet The, Lancet Limited. London, GB, vol. 361, No. 9371, May 24, 2003, pp. 1810-1812.
Guzick et al: "Polycystic ovary syndrome: Symptomatology, pathophysiology, and epidemiology" American Journal of Obstetrics & Gynecology, Mosby, St Louis, MO, US, vol. 179, No. 6, Dec. 1998, pp. S89-S93.
Lemay A et al: "Rosiglitazone and ethinyl estradiol/cyproterone acetate as single and combined treatment of overweight women with polycystic ovary syndrome and insulin resistance", Human Reproduction (Oxford), vol. 21, No. 1, Jan. 2006, pp. 121-128.
Ibanez Lourdes et al: "Flutamide-metformin plus ethinylestradiol-drospirenone for lipolysis and antiatherogenesis in young women with ovarian hyperandrogenism: The key role of metformin at the start and after more than one year of therapy" Journal of Clinical Endocrinology & Metabolism, vol. 90, No. 1, Jan. 2005, pp. 39-43.
Ibanez Lourdes et al: "High neutrophil count in girls and women with hyperinsulinaemic hyperandrogenism: normalization with metformin and flutamide overcomes the aggravation by oral contraception", Human Reproduction (Oxford), vol. 20, No. 9, Sep. 2005, pp. 2457-2462.
Vrbikova J et al: "Combined oral contraceptives in the treatment of polycystic ovary syndrome", Human Reproduction Update, vol. 11, No. 3, May 2005, pp. 277-291.
Guido M et al:. "Drospirenone for the treatment of hirsute women with polycystic ovary syndrome: A clinical, endocrinological, metabolic pilot study", Journal of Clinical. Endocrinology & Metabolism, vol. 89, No. 6, Jun. 2004, pp. 2817-2823.
English Language Abstract for DE 10 2004 026 679, 2005.
Ibanez Lourdes et al: Flutamide-metformin plus an oral contraceptive (OC) for young women with polycystic ovary syndrome: switch from third-to-fourth-generation OC reduces body adiposity. In: Human Reproduction, 2004, 19(8), pp. 1725-1727.

* cited by examiner

*Primary Examiner* — Rei-tsang Shiao
(74) *Attorney, Agent, or Firm* — Norris McLaughlin & Marcus PA

(57) ABSTRACT

The present invention relates to a medicament which contains as the active ingredient combination at least one gestagen with a contraceptive action as the sole hormone component and at least one insulin sensitizer, which medicament is in particular suitable for preventing or treating pathological disorders which are caused by polycystic ovary syndrome (PCOS).

20 Claims, No Drawings

COMBINATION OF GESTAGEN AND INSULIN SENSITIZER FOR TREATING PCOS

This application is a Continuation Application of PCT/EP2007/004700 filed May 26, 2007, which claims priority to the German application 10 2006 026 026.0 filed Jun. 1, 2006.

The present invention relates to a medicament which contains as the active ingredient combination at least one gestagen with a contraceptive action as the sole hormone component and at least one insulin sensitiser, which medicament is in particular suitable for preventing or treating pathological disorders which are caused by polycystic ovary syndrome (PCOS).

With a prevalence of 5 to 10%, polycystic ovary syndrome (PCOS) is one of the commonest diseases of young women. Apart from polycystic ovaries, symptoms of this complaint as it progresses are oligomenorrhoea and amenorrhoea, symptoms of androgenisation, such as hirsutism, acne, alopecia and/or adiposity. Further sequelae of this complaint which are observed include increasing insulin resistance and thus a risk of type II diabetes mellitus, ovulatory dysfunction or even infertility, a greatly increased risk of suffering from endometrial carcinoma, endometrial hyperplasia, ovarian cancer and/or breast cancer and from serious cardiovascular diseases, in particular a greatly increased risk of cardiac infarct.

Treatment of the pathological disorders caused by PCOS, involves not only combating obesity and achieving dramatic weight loss, but also prescribing taking of oestrogen-containing contraceptives and/or insulin sensitisers, such as metformin.

It is, however, also known that taking oestrogen-containing contraceptives, at least over the long term, cannot be completely dissociated from the risk of cardiovascular diseases and/or breast cancer.

There is thus a requirement to provide a medicament which may be used for preventing or treating pathological disorders and long-term sequelae caused by polycystic ovary syndrome without increasing the risk of cardiovascular and/or neoplastic diseases.

The object is achieved according to the invention by the provision of a medicament, the active ingredient combination of which consists of at least one gestagen with a contraceptive action as the sole hormone component and at least one insulin sensitiser.

The medicament according to the invention preferably contains as the sole hormonal component at least one gestagen with a contraceptive action selected from the group consisting of chlormadinone acetate, 3-β-OH-chlormadinone acetate (3β-hydroxy-6-chloro-17α-acetoxy-4,6-pregnadien-20-one), 3-α-hydroxy-chlormadinone acetate (3α-hydroxy-17α-acetoxy-4,6-pregnadien-20-one), 3α-hydroxy-17α-acetoxy-5β-pregnan-20-one, 3β-hydroxy-17α-acetoxy-5β-pregnan-20-one, 3-α-acetoxy-chlormadinone acetate, 3-β-acetoxy-chlormadinone acetate, dienogest, drospirenone, cyproterone acetate and mixtures of at least two of the stated gestagens, wherein the gestagens which are listed below as component d), e) or f), are not used as the sole gestagen or as the gestagen mixture f), but are instead used only in combination with a further, above-listed gestagen as the sole hormonal component in the active ingredient combination according to the invention. Antiandrogenic gestagens with a contraceptive action are particularly preferably used.

The medicament according to the invention contains as the insulin sensitiser component at least one compound selected from the group consisting of metformin, the physiologically acceptable salts thereof and glitazones. The glitazones used are preferably at least one glitazone selected from the group consisting of roseglitazone and pioglitazone and metformin hydrochloride is used as the salt of metformin. The stated active ingredients are commercially marketed products.

The medicament according to the invention is preferably provided as a dosage form with a specific number of daily units for uninterrupted, daily, oral administration to women, as is conventional for contraceptives.

Each of these daily units preferably comprises as the sole hormone component a gestagen content which at least corresponds to the ovulation inhibition dose of the gestagen component used, preferably is up to 150% above this ovulation inhibition dose. The corresponding ovulation inhibition dose is determined in known manner by the "Hoogland and Skouby" score.

Each daily unit preferably comprises the same quantity of the gestagen component. It is furthermore likewise particularly preferred for each daily unit to contain the same gestagen component. Particularly preferably, each daily unit comprises as the sole hormonal component chlormadinone acetate as the gestagen component or one of the following components a) to k), preferably in each case with the exception of component d), e) or f) alone:

a) 3α-hydroxy-chlormadinone acetate or
b) 3β-hydroxy-chlormadinone acetate or
c) a mixture of a) and b) in any desired mixing ratio or
d) 3α-hydroxy-17α-acetoxy-5β-pregnan-20-one or
e) 3β-hydroxy-17α-acetoxy-5β-pregnan-20-one or
f) a mixture of d) and e) in any desired mixing ratio or
g) a mixture of a) and/or b) with d) and/or e) in any desired mixing ratio or
h) a mixture of chlormadinone acetate (CMA) with a) and/or b) in a mixing ratio of 10 to 90 wt. % of CMA and 90 to 10 wt. % of a) and/or b), relative to the complete mixture, or
i) a mixture of chlormadinone acetate with d) and/or e) in a mixing ratio of 10 to 90 wt. % of chlormadinone acetate and 90 to 10 wt. % of d) and/or e), relative to the complete mixture, or
j) a mixture of chlormadinone acetate with c) and f) in a mixing ratio of 10 to 90 wt. % of chlormadinone acetate and 90 to 10 wt. % of c) and f), relative to the complete mixture, or
k) a mixture of chlormadinone acetate with g) in a mixing ratio of 10 to 90 wt. % of CMA and 90 to 10 wt. % of g), relative to the complete mixture.

Each daily unit preferably contains the same quantity of the gestagen component, wherein in order to ensure adequate contraceptive protection a daily unit is produced using 1 to 10 mg, preferably in each case at least 2 mg, particularly preferably in each case 2, 3, 4 or 5 mg of the gestagen component dienogest, cyproterone acetate, drospirenone, chlormadinone acetate, a mixture of at least 2 of the stated gestagens or one of components a) to k) in each case with the exception of component d), e) or f) alone.

Each daily unit preferably contains the same quantity of the insulin sensitiser component, wherein each daily unit particularly preferably also contains the same insulin sensitiser component. A daily unit preferably comprises 500 to 2000 mg, preferably 1000 to 1500 mg of metformin, preferably as metformin hydrochloride, and/or at least 2 to 45 mg of a glitazone, particularly preferably 15 to 30 mg of pioglitazone or particularly preferably 4 to 8 mg of roseglitazone.

The medicament according to the invention is suitable for preventing or treating pathological disorders which are caused by polycystic ovary syndrome (PCOS). The medicament according to the invention is particularly preferably suitable for preventing or treating insulin resistance, oligomenorrhoea or amenorrhoea, hyperandrogenaemia, type II diabetes mellitus (T2DM), cardiovascular diseases and/or for preventing endometrial carcinoma, endometrial hyperplasia, ovarian cancer and/or breast cancer in addition to a preferably contraceptive action. The medicament according to the invention is particularly preferably suitable for preventing or treating insulin resistance, type II diabetes mellitus, androgenic disorders, such as hirsutism, acne or alopecia, obesity, female infertility and/or cardiovascular diseases.

The present invention accordingly also provides the use of the above-listed active ingredient combinations consisting of at least one gestagen component with a contraceptive action as the sole hormone component and at least one insulin sensitiser for producing a medicament for preventing and/or treating the above-listed pathological disorders which are caused by polycystic ovary syndrome (PCOS).

To this end, the medicament according to the invention is preferably provided in a dosage form which comprises a specific number of daily units in the form of tablets which, in addition to the active ingredient combination according to the invention, optionally also contain conventional auxiliary substances.

The medicament according to the invention in the form of the above-described daily units may here be intended for uninterrupted, oral administration for uninterrupted administration over at least 28 successive days.

To ensure successful prevention and/or treatment of the pathological disorders caused by PCOS, the medicament according to the invention may also be provided in the form of daily units in a such number as is suitable for uninterrupted administration over two or more years, preferably for up to 2 years, particularly preferably for up to 1 year. It is here also possible to provide the medicament according to the invention in a dosage form whose maximum number of daily units is suitable for uninterrupted administration on 84 days or only on 56 days.

As has already been explained, the medicament according to the invention is preferably present as an oral dosage form, very particularly preferably in the form of tablets. A daily unit here corresponds in each case to one tablet. The tablets are preferably packaged in accordance with a tablet-taking cycle in blister packs and are preferably provided, with an indication of the daily unit to be taken, as medicament package containing at least one such blister pack for the prescribed, uninterrupted administration. A kit preferably comprises at least 3 blister packs having in each case 28 daily units in a medicament package.

EXAMPLES

Example 1

Composition

|  | Per tablet |
| --- | --- |
| Metformin · HCl | 1000 mg |
| Chlormadinone acetate | 3 mg |
| Povidone K30 | 40 mg |
| Microcrystalline cellulose | 201 mg |
| Crospovidone | 40 mg |
| Magnesium stearate | 8 mg |
| Highly disperse silicon dioxide | 8 mg |

Povidone K 30 (polyvinylpyrrolidone, PVP) was dissolved in a sufficient quantity of water. Chlormadinone acetate (particle size 90%<50 μm), microcrystalline cellulose, metformin.HCl and crospovidone were mixed in a mixer/pelletiser (Diosna P25) for 5 mins and then moistened thoroughly and mixed with the aqueous PVP solution. The moist composition was forced through a 3 mm screen and dried in a vacuum drying cabinet. The dried granular product was disagglomerated through a 1.0 mm screen, mixed with magnesium stearate and highly disperse silicon dioxide and pressed into oblong tablets (9×21 mm) with a weight of 1300 mg.

The tablets were coated with a methylhydroxypropylcellulose-based coating (e.g. Opadry YS-1-2184); coating mass 20 mg per tablet.

28 of these tablets were packaged in a blister pack marked with days as hormone-containing daily units to provide a dosage form used according to the invention.

Example 2

Composition

|  | Per tablet |
| --- | --- |
| Pioglitazone | 15 mg |
| Chlormadinone acetate | 3 mg |
| Povidone K30 | 5 mg |
| Lactose | 55 mg |
| Maize starch | 20 mg |
| Magnesium stearate | 1 mg |
| Highly disperse silicon dioxide | 1 mg |

Povidone K 30 (polyvinylpyrrolidone, PVP) was dissolved in a sufficient quantity of water. Chlormadinone acetate (particle size 90%<50 μm), lactose, pioglitazone and maize starch were mixed in a mixer/pelletiser (Diosna P25) for 5 mins and then moistened thoroughly and mixed with the aqueous PVP solution. The moist composition was forced through a 3 mm screen and dried in a vacuum drying cabinet. The dried granular product was disagglomerated through a 0.6 mm screen, mixed with magnesium stearate and highly disperse silicon dioxide and pressed on a tablet press with 7 mm punches into tablets with a weight of 100 mg.

The tablets were coated with a methylhydroxypropylcellulose-based coating (e.g. Opadry YS-1-2184); coating composition 2 mg per tablet 28 of these tablets were packaged in a blister pack marked with days as hormone-containing daily units to provide a dosage form used according to the invention.

The invention claimed is:

1. A medicament consisting of an active ingredient combination and one or more conventional auxiliary substances, wherein the active ingredient combination consists of at least one insulin sensitizer and at least one an antiandrogenic gestagen component, wherein the antiandrogenic gestagen component is chlormadinone acetate or selected from the group consisting of:
   a) 3α-hydroxy-chlormadinone acetate;
   b) 3β-hydroxy-chlormadinone acetate;
   c) a mixture of a) and b) in any desired mixing ratio;
   d) 3α-hydroxy-17α-acetoxy-5β-pregnan-20-one;
   e) 3β-hydroxy-17α-acetoxy-5β-pregnan-20-one;
   f) a mixture of d) and e) in any desired mixing ratio;
   g) a mixture of a) and/or b) with d) and/or e) in any desired mixing ratio;

h) a mixture of chlormadinone acetate (CMA) with a) and/or b) in a mixing ratio of 10 to 90 wt. % of CMA and 90 to 10 wt. % of a) and/or b), relative to the complete mixture;

i) a mixture of chlormadinone acetate with d) and/or e) in a mixing ratio of 10 to 90 wt. % of chlormadinone acetate and 90 to 10 wt. % of d) and/or e), relative to the complete mixture;

j) a mixture of chlormadinone acetate with c) and f) in a mixing ratio of 10 to 90 wt. % of chlormadinone acetate and 90 to 10 wt. % of c) and f), relative to the complete mixture;

k) a mixture of chlormadinone acetate with g) in a mixing ratio of 10 to 90 wt. % of CMA and 90 to 10 wt. % of g), relative to the complete mixture; and mixtures thereof, wherein components d), e) or f), listed above, are not used as the sole gestagen or as the gestagen mixture in f), but are instead used only in combination with a further, above-listed gestagen.

2. A medicament according to claim 1 wherein the insulin sensitizer is selected from the group consisting of metformin, the physiologically acceptable salts of metformin and glitazones.

3. A medicament according to claim 2 wherein the insulin sensitizer is selected from the group consisting of roseglitazone, pioglitazone, -metformin hydrochloride and mixtures thereof.

4. A medicament according to claim 1 wherein the medicament is present as a dosage form with a specific number of daily units intended for uninterrupted, deity, oral administration to women.

5. A medicament according to claim 4, wherein the anti-androgenic gestagen content in each daily unit corresponds to the ovulation inhibition dose of the gestagen.

6. A medicament according to claim 5, wherein each daily unit consists of the same quantity of the gestagen component.

7. A medicament according to claim 1 wherein each daily unit consists of the same gestagen component.

8. A medicament according to claim 4 wherein a daily unit consists of chlormadinone acetate in a quantity of 1.5 to 10 mg.

9. A medicament according to claim 8 wherein each daily unit of a dosage form consists of chlormadinone acetate in each case uniformly in a quantity of 2, 3, 4, or 5 mg.

10. A medicament according to claim 4 wherein each daily unit consists of the same quantity of the insulin sensitiser component.

11. A medicament according to claim 10, wherein each daily unit consists of metformin in a quantity of 500 to 2000 mg.

12. A medicament according to claim 4 wherein each daily unit consists of the same insulin sensitiser component.

13. A medicament according to claim 4 wherein the dosage form consists of at least 28 daily units.

14. A medicament according to claim 13, wherein the maximum number of daily units of a dosage form corresponds to uninterrupted administration for two or more years.

15. A medicament according to claim 13 wherein the maximum number of daily units of a dosage form corresponds to uninterrupted administration for 84 days.

16. A medicament according to claim 5 wherein the anti-androgenic gestagen content in each daily unit is up to 150% above the ovulation inhibition dose of the gestagen component.

17. A medicament according to claim 11 further consists of at least one glitazone in a quantity of 2 to 30 mg.

18. A medicament according to claim 12 wherein the maximum number of daily units of a dosage form corresponds to uninterrupted administration for 1 year.

19. A method for treating pathological disorders caused by polycystic ovary syndrome (PCOS), wherein the disorders are selected from a group consisting of insulin resistance, androgenic disorders, female infertility, oligomenorrhoea, amenorrhoea, hyperandrogenaemia, type II diabetes mellitus (T2DM), cardiovascular diseases, endometrial hyperplasia, mammary carcinoma, ovarian cancer and endometrial carcinoma, comprising the step of administering to a person a pharmaceutical dosage form of the medicament according to claim 1.

20. A method according to claim 19 wherein the administration of the dosage form results in simultaneous contraception.

* * * * *